United States Patent
Ichikawa et al.

(10) Patent No.: US 7,160,488 B2
(45) Date of Patent: Jan. 9, 2007

(54) METHOD OF MANUFACTURING INTRAOCULAR LENSES AND INTRAOCULAR LENSES MANUFACTURED BY THE METHOD

(75) Inventors: Ken Ichikawa, Aichi (JP); Yoshihiro Nakahata, Gamagori (JP); Tsutomu Sunada, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 409 days.

(21) Appl. No.: 10/646,705

(22) Filed: Aug. 25, 2003

(65) Prior Publication Data

US 2004/0041289 A1 Mar. 4, 2004

(30) Foreign Application Priority Data

Aug. 30, 2002 (JP) .............................. 2002-253945

(51) Int. Cl.
*B29D 11/00* (2006.01)
(52) U.S. Cl. ......................................... 264/1.1; 264/2.6
(58) Field of Classification Search ................. 264/1.1, 264/1.7, 2.6, 236; 623/5.11, 6.11; 425/808
See application file for complete search history.

(56) References Cited

U.S. PATENT DOCUMENTS 4,834,750 A 5/1989 Gupta 5,290,892 A * 3/1994 Namdaran et al. ........... 526/259
5,296,305 A * 3/1994 Baude et al. ................ 428/520

FOREIGN PATENT DOCUMENTS

| EP | 0 552 528 A1 | 7/1993 |
| FR | 2 779 940 | 12/1999 |
| JP | A 1-158949 | 6/1989 |
| JP | A 10-192311 | 7/1998 |
| JP | A 2002-17845 | 1/2002 |
| WO | WO 99/29750 | * 6/1999 |

* cited by examiner

*Primary Examiner*—Mathieu D. Vargot
(74) *Attorney, Agent, or Firm*—Oliff & Berridge, PLC

(57) ABSTRACT

A method of manufacturing an intraocular lens includes: a first step of producing a base material for the intraocular lens by polymerizing a first polymerizable monomer which is a raw material of the base material; a second step of producing a monomer-impregnated base material by impregnating the base material produced in the first step with a second polymerizable monomer; a third step of setting a protective member on a surface of the base material produced in the second step to prevent the surface of the base material from drying; and a fourth step of polymerizing the second polymerizable monomer impregnated in the base material on which the protective member is set.

3 Claims, 4 Drawing Sheets

METHOD OF MANUFACTURING INTRAOCULAR LENSES AND INTRAOCULAR LENSES MANUFACTURED BY THE METHOD

FIELD OF THE INVENTION

The present invention relates to a method of manufacturing an intraocular lens and an intraocular lens manufactured by the method.

DESCRIPTION OF RELATED ART

As one of cataract operation methods, there has commonly been used a method of implanting an intraocular lens in place of a crystalline lens (lens nucleus) after extracting the crystalline lens. Such method includes the following steps of making an incision in an eyeball of a patient's eye for inserting therethrough the intraocular lens; fragmenting and aspirating a clouded crystalline lens of the eye through the incision by means of an ultrasonic cataract-surgery device or the like; and inserting the intraocular lens into the eye through the incision to implant the intraocular lens in a place where the crystalline lens once lay.

Such intraocular lenses include a hard-type intraocular lens made of PMMA (polymethyl methacrylate) or the like and a soft-type intraocular lens made of acrylic or the like, which is foldable. These intraocular lenses can be manufactured by a method (a cast molding method) of injecting a raw material monomer into a casting mold having a desired lens shape and then polymerizing and curing the monomer material or another method (a lathe cutting method) of cutting a sheet obtained by polymerization and cure of a raw material monomer into an intraocular lens having a desired shape.

However, it has been reported that the intraocular lenses manufactured by the above methods caused some problems due to voids formed in a base material for an intraocular lens, the base material being produced by the polymerization and cure.

For instance, it has been reported that in the soft-type intraocular lens made of hydrophobic (or nonhydrous) soft acrylic, many small luminescent or bright spots called glistenings appeared in an optic part (a lens part) of the intraocular lens after implanted in an eye. A report says that the occurrence of luminescent spots does not affect minimum resolution, so-called visual acuity, whereas it may affect contrast sensitivity, and surmises that such occurrence of luminescent spots would be caused by the aqueous humor having entered voids formed in the intraocular lens (the base material).

Furthermore, the soft-type intraocular lens made of hydrophilic (hydrous) soft acrylic has a problem that proteins and others are apt to enter the voids formed in the intraocular lens (the base material) after implanted in the eye, which may lower the transparency of the intraocular lens.

SUMMARY OF THE INVENTION

The present invention has been made in view of the above circumstances and has an object to overcome the above problems and to provide a method of manufacturing an intraocular lens, capable of preventing the formation of voids in a lens base material while keeping a good lens material condition, and an intraocular lens manufactured by the method.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, the present invention provides a method of manufacturing an intraocular lens including: a first step of producing a base material for the intraocular lens by polymerizing a first polymerizable monomer which is a raw material of the base material; a second step of producing a monomer-impregnated base material by impregnating the base material produced in the first step with a second polymerizable monomer; a third step of setting a protective member on a surface of the base material produced in the second step to prevent the surface of the base material from drying; and a fourth step of polymerizing the second polymerizable monomer impregnated in the base material on which the protective member is set.

According to another aspect of the present invention, there is provided a method of manufacturing an intraocular lens including: a first step of producing a base material for the intraocular lens by polymerizing a first polymerizable monomer which is a raw material of the base material; a second step of impregnating the base material produced in the first step with a second polymerizable monomer; and a third step of polymerizing the second polymerizable monomer impregnated into the base material in the second step.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
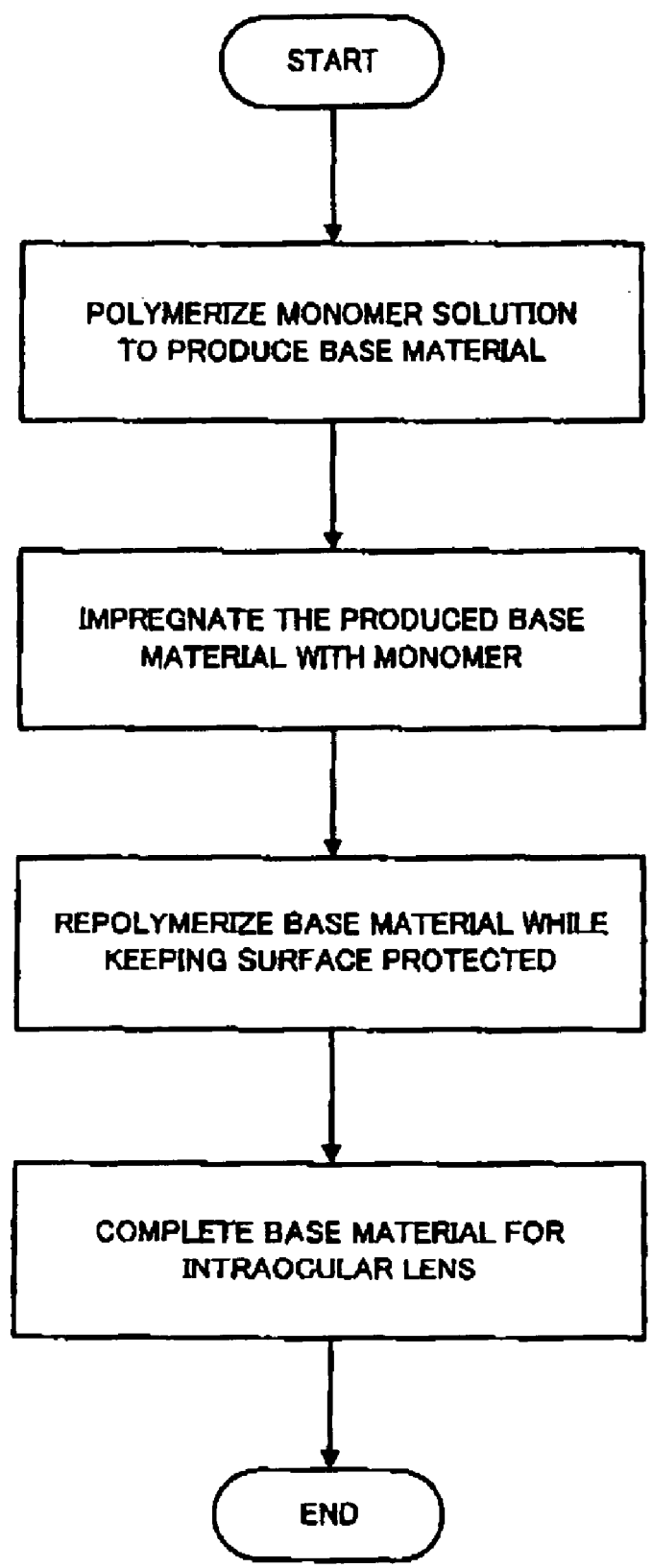
FIG. 1 is a flowchart showing a flow of a manufacturing method of an intraocular lens in a present embodiment.

A detailed description of a preferred embodiment of an intraocular lens manufacturing method and an intraocular lens manufactured by the method, embodying the present invention will now be given referring to the accompanying drawings.

In the present embodiment, a lens base material is produced by polymerization and cure of a monomer solution which is a raw material used for an intraocular lens of a hydrophobic soft type, and the base material is immersed in the monomer solution, thereby impregnating the base material with the monomer. The base material after impregnated with the monomer is polymerized again to prevent the formation of voids in the base material.

The base material for the hydrophobic soft intraocular lens can be made of a single monomer or a mixture of plural kinds of monomers, the monomers being capable of forming a soft material. To regulate the hardness (softness) of the base material, a monomer capable of forming a hard material may be added as appropriate.

Concrete examples of the monomer for a soft material (hereinafter, referred to as a soft monomer) include acrylic ester such as methyl acrylate, ethyl acrylate, propyl acrylate, 2-ethylhexyl acrylate, butyl acrylate, or the like.

Concrete examples of the monomer for a hard material (hereinafter, referred to as a hard monomer) include methacrylic acid ester such as methyl methacrylate, ethyl methacrylate, propyl methacrylate, butyl methacrylate, or the like.

In the case where a base material is made of the above soft monomer or the mixture of the soft monomer and the hard monomer, a cross-linking agent and a polymerization initiator may be added as necessary. To be more precise, the cross-linking agent may be selected from any materials usable as a cross-linking agent for production of the base material for an intraocular lens, for example, dimethacrylate ester such as ethylene glycol dimethacrylate, diethylene glycol dimethacrylate, triethylene glycol dimethacrylate, or the like. The cross-linking agent is used in an amount of 0.5 to 10 wt % based on the total weight of the monomer(s) forming a base material. The polymerization initiator may be selected from any materials usable as a polymerization initiator for production of the base material for an intraocular lens, for example, azobisisobutyronitrile, azoisobutyrovaleronitrile, benzoin, methyl orthobenzoyl benzoate, etc. In addition to above, an ultraviolet absorber may be added as appropriate to impart an ultraviolet absorption effect to the base material.

In the present embodiment, the base material made of the above mentioned monomers, cross-linking agent, and polymerization initiator is immersed again in a monomer solution, thereby to impregnate the base material with the monomer. The monomer to be impregnated into the base material is used to fill the voids formed in the base material. Accordingly, the monomer is not particularly limited and may be any monomer if only it is polymerizable and good in biocompatibility. However, the same monomer (or mixture if several kinds of monomers are used in combination to make the base material) as that used for the production of the base material is preferably used to minimize the changes in physical properties of the produced base material. The monomer solution used in this case is also added with the above mentioned cross-linking agent and polymerization initiator of respective predetermined amounts.

<Manufacture of an Intraocular Lens>

Next, a method of manufacturing an intraocular lens using the above mentioned monomers and others is explained with reference to a flowchart in FIG. 1. This explanation is here made on a 3-piece type intraocular lens as an example. This lens is constructed of an optical part and support parts which are separately produced and then assembled into one body.

In this embodiment, a soft monomer, a hard monomer, and a cross-linking agent are injected into a vessel so that they are mixed at a predetermined ratio. The mixing ratio between the soft monomer and the hard monomer to form a copolymer is selectively determined according to respective physical properties. This mixing ratio may be a ratio at which a finished intraocular lens can have so hardness (softness) as to permit the lens to be folded in a surgical operation.

After completion of mixing of the soft monomer, hard monomer, and cross-linking agent, a polymerization initiator is added and mixed with the mixture. Successively, this monomer mixed solution is poured into a casting mold having a flat-plate-shape and polymerized in a water bath at a temperature between 50° C. and 70° C. for 12 to 36 hours, and then polymerized in a dry oven at a temperature between 80° C. and 100° C. for 12 to 36 hours. Such stepwise increasing of the temperature enables more stable polymerization. After that, the flat-plate-shaped base material is taken out from the casting mold and is further put in a vacuum oven and left standing at a temperature between 80° C. and 120° C. for 12 to 36 hours. Thus, polymerization is completed.

Subsequently, the produced base material is fully immersed in a vessel filled with the monomer mixed solution having the same composition as above and left standing for a predetermined time to impregnate the base material with the monomer. At this time, when the base material is simply put in the vessel for impregnation with the monomer, the lower surface of the material is brought into close contact with the bottom of the vessel. Accordingly, the base material could become difficult to impregnate through the lower surface with the monomer. The impregnation of the base material with the monomer through the upper surface of the base material is more caused than through the lower surface, which likely results in the occurrence of warps or cracks of the base material. On this account, the base material is uniformly impregnated with the monomer through the whole areas of the surfaces, thereby preventing the occurrence of warps or cracks.

Figure 2:
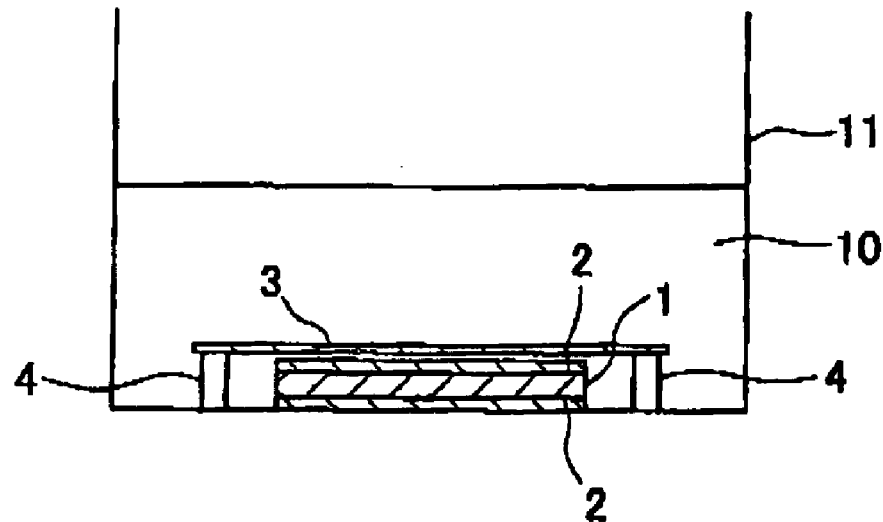
FIG. 2 is a view showing a structure for impregnating a base material for the intraocular lens through a whole surface thereof with a monomer.

FIG. 2 is a view showing a structure for impregnating the base material with a monomer equally through the upper and lower surfaces. Numeral 1 is a base material having surfaces (upper and lower surfaces) on which absorptive members 2 of a sheet form capable of absorbing a monomer mixed solution 10 are set to entirely cover each surface so that the base material 1 is sandwiched between the absorptive members 2. As this absorptive member 2, anything may be adopted if it is capable of absorbing the monomer mixed solution 10 and insoluble in this monomer mixed solution 10. For example, a paper filter may be used.

When the base material 1 on which the absorptive members 2 are set is placed at the bottom of a vessel 11 filled with the monomer mixed solution 10, the lower surface of the base material 1 is not in direct contact with the bottom of the vessel 11. Thus, the monomer mixed solution 10 is allowed to be impregnated into the base material 1 through the whole areas of the surfaces (upper and lower surfaces) of the base material 1 by way of the absorptive members 2. As a result, warps and cracks can be prevented from occurring due to the impregnation of the base material 1 with the monomer mixed solution 10.

To further prevent the warps of the base material, a glass plate 3 is disposed above the base material 1 placed at the bottom of the vessel 11. This glass plate 3 is supported by spacers 4 so as to be in contact with the absorptive member 2 set on the upper surface of the base material 1 or so as to have a slight clearance with respect to the absorptive member 2. Laying the glass plate 3 in such a position can prevent the warps from progressing even in case that the base material 1 starts to warp.

In the present embodiment, as shown in FIG. 2, the absorptive members 2 are not set on the side surfaces (defining the thickness) of the base material 1, but they may be added thereon. However, since the side surfaces of the base material 1 are extremely small in area as compared with the upper and lower surfaces, there is little influence even where no absorptive member 2 is set on the side surfaces.

In the present embodiment, as above, the absorptive members 2 are in contact with the surfaces of the base material 1 as shown in FIG. 2. Alternatively, any structure may be adopted if it allows to uniformly impregnate the base material 1 with the monomer mixed solution 10 through the whole area of the surfaces. For instance, the absorptive member 2 may be set on only the lower surface of the base material 1. The base material 1 may be supported at a predetermined height in the monomer mixed solution 10 or at a predetermined spacing from the bottom of the vessel 11, so that the base material 1 is impregnated with the monomer mixed solution 10 through the whole area of the surfaces.

The time for impregnation of the base material 1 in the monomer mixed solution 10, which varies according to the shape of the base material 1 and peripheral conditions (temperature, atmospheric pressure, etc.), is determined at the time needed to impregnate the voids formed in the base material 1 with the monomer mixed solution 10.

Specifically, the time for impregnation is set in a range of 24 hours to 120 hours, more preferably, 48 hours to 96 hours. If this time is less than 24 hours, it would be difficult to sufficiently fill voids formed in the base material 1 with the monomer mixed solution 10. Although the time may be 120 hours or more, the longer time would reduce production efficiency.

Figure 3:
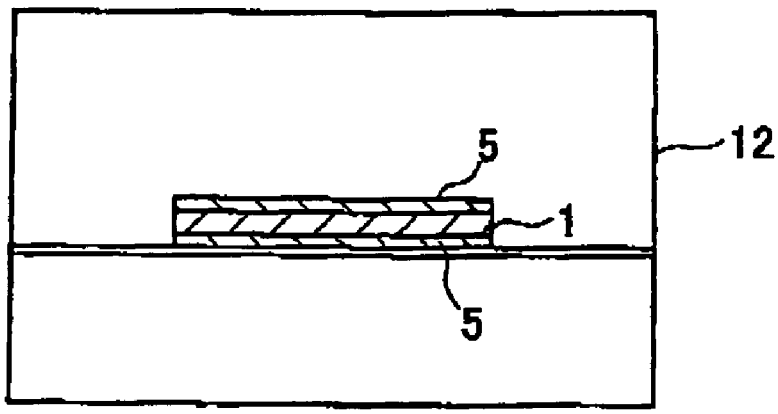
FIG. 3 is a view showing a manner of repolymerizing the base material.

After immersion of the base material 1 in the monomer mixed solution 10 for the predetermined time, thus impregnating the base material 1 with the monomer mixed solution 10, the base material 1 is taken out therefrom. Then, the absorptive members 2 are taken off from the base material 1, and this base material 1 is wiped to remove the monomer mixed solution 10 from the surface. Thereafter, the base material 1 is repolymerized. FIG. 3 is a view showing a manner of repolymerizing the base material 1.

Numeral 5 is a protective member of a sheet form which is set (attached) on the surface (upper and lower surfaces) of the base material 1 to prevent drying of the surface. This protective member 5 may be made of any material resistant to the monomer mixed solution 10 and also heat. The protective member 5 is preferably a member which is useful to find or detect the air remaining between the base material 1 and the protective member 5 and has a certain degree of flexibility enough to remove the air therefrom. The protective member 5 used in the present embodiment is a glass plate having a thickness of about 1 mm. This glass plate enables a worker to find the air remaining between the base material 1 and the protective member 5 and to push out the air by pressing the glass plate from the outside. Such protective member 5 may be for example aluminum foil besides the glass plate.

Numeral 12 is a dry oven. In this oven 12, the base material 1 on which the protective members 5 are set in contact relation is placed and heated for a predetermined time to cause the second polymerization (repolymerization). The heating temperature to the base material 1 in the oven 12 is preferably in a range of 70° C. to 120° C., more preferably, 80° C. and 100° C. The heating time is 12 to 48 hours, more preferably, 18 to 36 hours. The surfaces of the base material 1 are covered by the protective members 5 while the second polymerization of the base material 1 is performed in the dry oven 12, so that deformation, cracks, and the like, which are likely caused by sudden drying can be prevented.

After the second polymerization in the dry oven 12, the protective members 5 are removed (detached) from the base material 1. This base material 1 is then heated in a vacuum oven for a predetermined time, thereby bringing polymerization to completion. The heating temperature in the vacuum oven is preferably in a range of 70° C. to 120° C., more preferably, 80° C. and 100° C. The heating time is 12 to 48 hours, more preferably, 18 to 36 hours.

In the above manner, the base material produced by the first polymerization is impregnated with the monomer for the second polymerization, so that the voids formed in the base material through the first polymerization can be filled.

Subsequently, the base material produced by such two-stage polymerization is cut into a desired lens shape by a well known cutting process, thus making an intraocular lens. In order to make a 3-piece type intraocular lens, for example, the produced base material is cut into a lens shape and ground, thereby forming a lens part (an optic part) of the 3-piece type intraocular lens. Then, support parts (haptic parts) formed by a well known manufacturing process are welded to the lens part. The finished intraocular lens is thus obtained.

Figure 4:
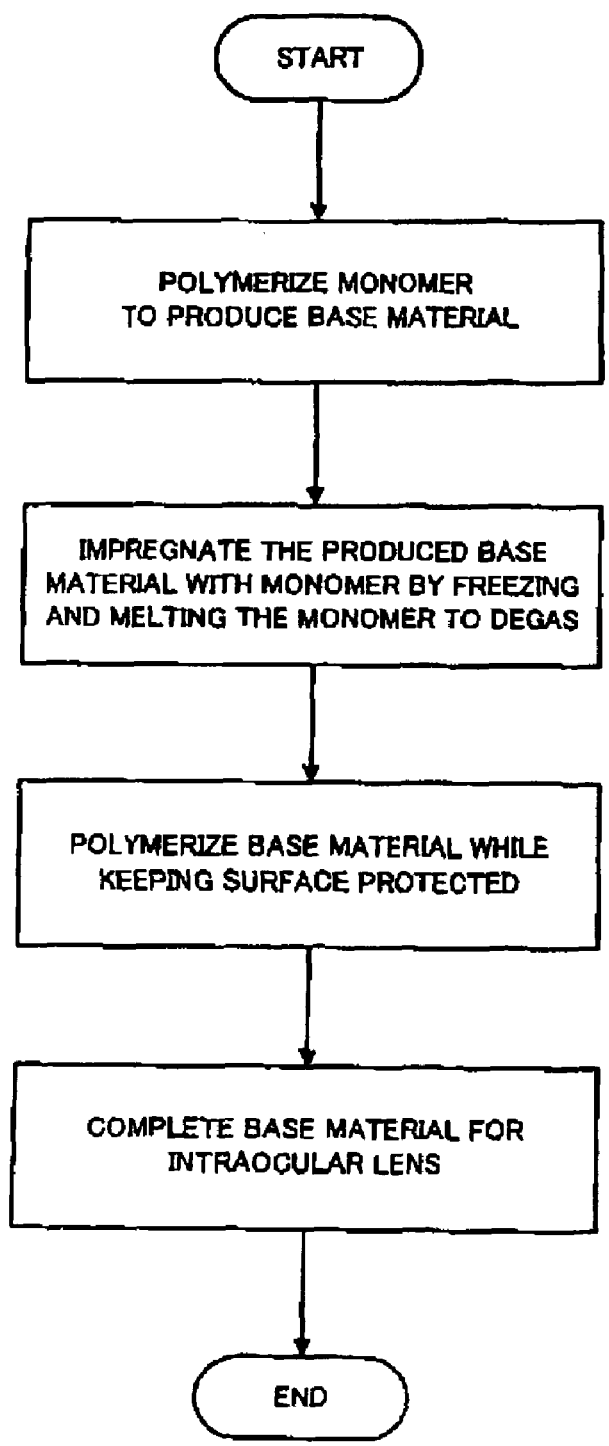
FIG. 4 is a flowchart showing another manufacturing method of an intraocular lens in the present embodiment.

It is to be noted that the method of impregnating the base material with the monomer is not limited to the above mentioned method. For example, as shown in a flowchart in FIG. 4, when the base material is impregnated with the monomer while freezing and melting the monomer to remove gases from the monomer (a degassing operation), the voids in the base material can further be reduced.

To be concrete, the base material obtained after the first polymerization and the monomer solution are put in a sealed container which can be vacuumized. The container internally holding the base material and the monomer solution is immersed in a freezing medium such as liquid nitrogen, freezing the monomer solution. Then, the container is taken out from the freezing medium, and a vacuum pump or the like is used to reduce the inside pressure of the container, thereby performing the degassing operation. This degassing is continued until the monomer solution is melted. The above freezing and melting operation is repeated several times and finally the sealed container is left standing for a predetermined time under the reduced pressure to sufficiently impregnate the base material with the monomer. This time for leaving the container to stand may be set in a range of 24 hours to 120 hours. Thereafter, the base material is taken out from the sealed container. The surface of the base material is wiped to remove the monomer therefrom. The above operations are performed using the dry oven and the vacuum oven to completely terminate polymerization. Subsequently, the produced base material is cut into a desired lens shape by a cutting process to finish an intraocular lens.

In the present embodiment, the base material after polymerized twice is shaped into an intraocular lens by the cutting process. The present invention is not limited thereto and may be applied to an intraocular lens manufactured by for example a cast molding method. In this case, the following steps are performed; a monomer solution injected into a casting mold having a desired lens shape is polymerized to produce a base material; this base material is formed in a lens shape and immersed into a monomer solution (preferably, having the same composition as that of the monomer solution used for forming the base material); and the monomer impregnated into the base material is polymerized. When the monomer impregnated into the base material is polymerized, possible swelling might cause changes in shape and refractive index of the base material. Accordingly, the degrees of such changes are preferably considered in advance in preparing a casting mold whereby a finished lens having a desired refractive index can be manufactured. In this case, as in the above case, the base material is constructed to allow impregnation through the whole areas of the surfaces thereof with the monomer, and the base material is heated for repolymerization in a state that the surfaces are covered by the protective members. Thus, it is possible to keep the base material in a good condition and prevent voids from being formed in the base material.

In the present embodiment, the hydrophobic soft-type intraocular lens is exemplified to explain the manufacturing method thereof, but the present invention is not limited thereto. The method according to the present invention can be used to fill the voids formed in the base material with the polymerizable monomer, regardless of the physical properties of the base material. The present method can also be applied to a hydrophilic soft-type intraocular lens made of for example 2-hydroxyethyl methacrylate, vinyl pyrolidone, etc.

<Glistening Inspection>

Figure 5:
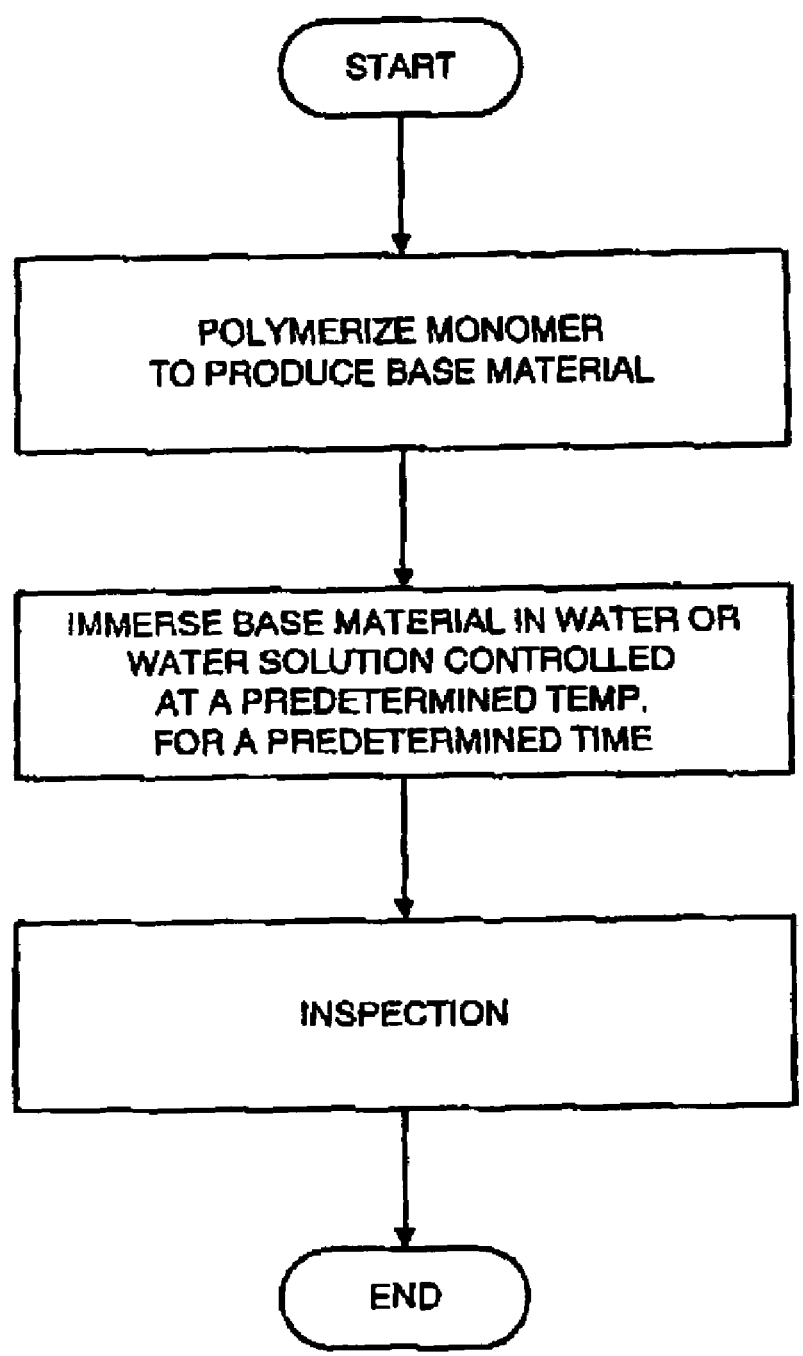
FIG. 5 is a flowchart showing a flow of a method for inspecting the degree of formation of voids in the base material.

Next, the base material produced by the two-stage polymerization in the present embodiment and other base materials produced by different methods are inspected to check the degree of occurrence of glistenings (luminescent spots) in each base material. The method of inspecting (evaluating) the degree of formation of voids in each base material (namely, the void formation state) is explained below with reference to a flowchart in FIG. 5.

The inspection to check the occurrence degree of luminescent spots is carried out as below by using the base material produced by the above intraocular lens manufacturing method. The base material produced by the two-stage polymerization is cut into disks each having a substantive intraocular lens shape (10 mm in diameter and 1 mm in thickness in the present embodiment). These disks (base materials) are immersed in constant temperature water bathes controlled at constant temperatures, and the disks are left standing in the bathes for respective predetermined times.

The water solution filled in the above constant temperature water bathes is preferably saline, Ringer's solution, and others, which are close to bodily fluid in order to establish a similar environment to an intraocular condition. However, the water solution may be pure water, tap water, or the like because the present inspection only requires to observe the formation state of voids in the disk (base material).

The water temperature in each constant temperature water bath is preferably in a range of 40° C. to 70° C., more preferably, 45° C. to 60° C. If the water temperature is lower than 40° C., it becomes difficult to intentionally generate luminescent spots. If the water temperature exceeds 70° C., on the other hand, luminescent spots would occur rapidly and therefore it becomes difficult to compare occurrence degrees of luminescent spots between disks (base materials).

The time for immersion of the disks (base materials) in each water bath is preferably in a range of 20 min. to 120 min., more preferably 30 min. to 60 min. If the immersion time is less than 20 min., the disk (base material) could not sufficiently be impregnated with water. The immersion time may exceed 120 min; however, as the immersion time becomes longer than 120 min., it will take a much time to get through the inspection, which reduces the inspection efficiency.

After immersion in each water bath for a predetermined time, the disk (base material) is taken out together with the constant temperature water to room temperature, and variations of the disk (base material) with time is immediately observed through a microscope. If the disk (base material) alone is taken out from the water bath and then observed through the microscope, luminescent spots would occur very fast, which makes it difficult to properly evaluate each base material. In order to cause the luminescent spots to occur at an appropriate speed, it is preferable to take out each disk (base material) together with the constant temperature water and observe the variations with time through the microscope. This makes it possible to more conveniently evaluate each disk (base material). The occurrence degree of luminescent spots varies with time according to time (duration) and temperature for immersion of each disk (base material) in the constant temperature water.

According to the above inspection method, the occurrence degree of luminescent spots in each base material can be observed with time. Consequently, the amount of voids formed in each base material can roughly be grasped based on the number of the luminescent spots that occurred in each base material and the occurrence speed of those luminescent spots. It is therefore possible to evaluate the appropriateness of each base material for an intraocular lens.

In the present embodiment, the base material is inspected before finishing an intraocular lens. Alternatively, the same inspection method as above may also be used with respect to a finished intraocular lens to inspect glistenings and the formation degree of voids in each lens.

The occurrence degree of luminescent spots with respect to the temperature and time (duration) for immersion is shown in Table 1. This table represents the results of study of preferable conditions for intentionally generating luminescent spots in each base material.

The raw materials used for the base material include 162.0 parts by weight of ethylene glycol phenyl ether acrylate and 12.0 parts by weight of n-butyl acrylate as a soft monomer, 119.1 parts by weight of n-butyl methacrylate as a hard monomer, 6.0 parts by weight of 1,4-butanediol diacrylate as a cross-linking agent, and 0.3 part by weight of azoisobutyronitrile as a polymerization initiator. Those raw materials are mixed and polymerized. The thus produced flat-plate-shaped base material was cut into disks each having a diameter of 10 mm and a thickness of 1 mm. Each disk was visually observed through a microscope (SMZ1500, manufactured by Nikon Corporation) to check luminescent spots that occurred in each disk in accordance with the above mentioned inspection method. The water in the constant temperature water bathes was pure water and the water temperatures in the bathes were set at 40° C., 45° C., 50° C., 60° C., and 70° C. respectively. For each water temperature, the immersion times were set at 10 min., 20 min., 30 min., 40 min., 50 min., 60 min., and 120 min. The inspection period was one hour from the time the disk was taken out from the water bath (i.e., an inspection start time).

TABLE 1

[Comparison of luminescent spots in each base material at different water temperatures and immersion times]

| | 10 (min.) | 20 | 30 | 40 | 50 | 60 | 120 |
|---|---|---|---|---|---|---|---|
| 40 (° C.) | X:x | X:x | X:x | X:x | X:x | X:x | X:Δ |
| 45 | X:x | X:x | X:x | X:Δ | ○ | ○ | ○ |
| 50 | X:x | X:Δ | X:Δ | ○ | ○ | ○ | Y:Δ |
| 60 | X:x | X:Δ | ○ | Y:Δ | Y:x | Y:x | Y:x |
| 70 | X:Δ | Y:Δ | Y:Δ | Y:x | Y:x | Y:x | Y:x |

X: Peripheral part, Y: Whole area

In Table 1, "X:x" indicates the case where no luminescent spot occurred in even the peripheral part of a disk even after one hour from the inspection start time, and "Y:x" indicates the case where luminescent spots occurred in the whole area of a disk immediately after the disk was taken out from the water bath. These cases are considered as conditions unable to be evaluated. "X:Δ" shows the case where luminescent spots occurred in only the peripheral part of a disk after one hour from the inspection start; however, it took a long time to cause the luminescent spots to occur, and "Y:Δ" shows the case where luminescent spots occurred in the whole area of a disk soon but not so fast as in the "Y:x" case. These cases are considered as conditions difficult to evaluate. Furthermore, "○" indicates that the occurrence degree of luminescent spots was moderate, which was a preferable condition to inspect the occurrence degree of luminescent spots in each disk (base material).

As shown in Table 1, in the case of the water temperature of 40° C., it was difficult to cause luminescent spots to occur even though the immersion time was changed, whereas it was possible to cause a few luminescent spots to occur when the immersion time was set at about 120 min. In the case of 45° C., it was possible to cause luminescent spots to moderately occur in a disk when the immersion time was set at 50 min. to 120 min., so that the occurrence degree of luminescent spots in each disk could be evaluated. In the case of 50° C., the immersion time of 40 min. to 60 min. was a preferable condition for the glistening inspection. In the case of 60° C., similarly, the immersion time of about 30 min. was a preferable condition for the glistening inspection. In the case of 70° C., the luminescent spots occurred immediately in the peripheral part of a disk when the immersion time was set at 10 min. and in the whole area of the disk when the immersion time was set at 20 min. or more, so that it was difficult to determine suitable conditions to cause luminescent spots to occur moderately.

It is to be noted that the inspection method described in the present embodiment allows evaluation for the appropriateness of using the base material to manufacture an intraocular lens, in about several hours, without the need for finishing the intraocular lens.

EXAMPLE 1

In Example 1, evaluations were made on the occurrence degree of luminescent spots in a base material for an intraocular lens, produced in the same producing method as the method described above in the present embodiment, except that the absorptive member such as a paper filter or the like was not used during the impregnation of the base material with the monomer and the protective member such as a glass plate or the like is not used during repolymerization of the base material in the dry oven. These evaluations were carried out by the glistening inspection mentioned above. This glistening inspection was performed under a condition considered preferable in Table 1, namely, at a water temperature of 45° C. and an immersion time of 60 min.

The raw materials used to produce the base material were the same as those used in the glistening inspection (i.e., 162.0 parts by weight of ethylene glycol phenyl ether acrylate, 12.0 parts by weight of n-butyl acrylate, 119.1 parts by weight of n-butyl methacrylate, 6.0 parts by weight of 1,4-butanediol diacrylate, and 0.3 part by weight of azoisobutyronitrile). The monomer solution used for immersing therein the base material was composed of the same materials as the raw materials of the base material.

In accordance with the intraocular lens manufacturing method mentioned above, the monomer solution was polymerized to produce a flat-plate-shaped base material. Then, this base material was immersed in a monomer solution composed of the same raw materials as those of the base material for 96 hours so that voids formed in the base material were filled with the monomer. The base material having been impregnated sufficiently with the monomer was taken out from the monomer solution and wiped to remove the monomer from the surface. The base material was then put in a dry oven at 90° C. for 24 hours to cause second polymerization. Furthermore, the base material was allowed to stand in a vacuum oven at 95° C. for 24 hours to complete the second polymerization The base material produced by the two-stage polymerization was cut into a disk having a diameter of 10 mm and a thickness of 1 mm. This disk was inspected by the above mentioned glistening inspection to check the occurrence degree of luminescent spots. The constant temperature water bath was previously filled with pure water controlled at 45° C., and the disk was immersed in the water bath for 1 hour. Thereafter, the disk was taken out together with the constant temperature water from the water bath to room temperature and immediately observed through the microscope to check variations with time. This observation was conducted to see the state of the disk after 10 min. and 60 min. respectively from the time the disk was taken out from the water bath. The observation results were shown in Table 2.

EXAMPLE 2

In Example 2, evaluations were made on the occurrence degree of luminescent spots in the base material produced by the method of impregnating the base material with the monomer by freezing and melting (without using the absorptive members and the protective members). The raw materials of the base material and the monomer solution used in this example were the same as those in Example 1.

The base material after the first polymerization and the monomer solution were put in a sealed container with a cock. The whole container was immersed in liquid nitrogen to completely freeze the monomer solution, and then the container was taken out from the liquid nitrogen. After that, a vacuum pump connected to the cock was operated to form a vacuum in the container, thereby performing a degassing operation. This degassing operation was continued until the frozen monomer solution was melted (fused). The freezing and melting were repeated three times and then the base material in the sealed container filled with the monomer solution was left standing for 96 hours under a reduced pressure. Subsequently, the base material was taken out from the sealed container and lightly wiped to remove the monomer from the surface. The base material was put in the dry oven at 90° C. for 24 hours to cause polymerization and was allowed to stand in the vacuum oven at 95° C. for 24 hours, thereby completing the polymerization.

The base material produced by the two-stage polymerization was cut into a disk having the same shape as that in Example 1 and then the glistening inspection was performed under the same conditions as in Example 1.

COMPARATIVE EXAMPLE 1

In Comparative example 1, evaluations were made on the occurrence degree of luminescent spots in a base material for an intraocular lens, produced in accordance with a conventional producing method (which differs only in the absence of the second polymerization from the method in Example 1). The raw materials of the base material were the same as those in Example 1. The produced base material was cut into a disk having the same shape as that in Example 1 and the glistening inspection was carried out under the same conditions as in Example 1.

TABLE 2

[Comparison in variations of each base material with time at a water temperature of 45° C. and an immersion time of 60 min.]

|  | 10 min. | 60 min. | Result |
| --- | --- | --- | --- |
| Example 1 | A few luminescent spots occurred in the peripheral part of a base material. | A larger number of luminescent spots occurred in the peripheral part as compared with those in the 10 min. case | ○ |
| Example 2 | Few luminescent spot was observed. | Few luminescent spot was observed. | ○ |
| Comp. Example 1 | Uncounted number of of luminescent spots occurred in | Uncounted numbers of luminescent spots occured | X |

TABLE 2-continued

[Comparison in variations of each base material with time at a water temperature of 45° C. and an immersion time of 60 min.]

| | 10 min. | 60 min. | Result |
|---|---|---|---|
| | the whole area of a base material, which was clouded. | in the whole area of base material, which was clouded. | |

(Results)

As compared with the base material in Comparative example 1, a very few luminescent spots occurred in the base materials in Examples 1 and 2. It was therefore evident that the intraocular lens manufacturing method according to the present invention was more effective to fill voids in the base material.

EXAMPLE 3

In Example 3, evaluations were made on a base material for an intraocular lens, produced by the producing method (using the absorptive members and the protective members) mentioned above in the present embodiment. These evaluations were carried out by an appearance check on the base material during impregnation with the monomer, another appearance check on the base material during repolymerization, and a glistening evaluation on the occurrence degree of luminescent spots in the base material. This glistening evaluation was performed by the above mentioned glistening inspection. The materials of the monomer solution used in this example were the same as those in Example 1.

In accordance with the intraocular lens manufacturing method mentioned above, the monomer solution was polymerized (immersion in a water bath at 60° C. for 24 hr; heating in a dry oven at 90° C. for 24 hr; and heating in a vacuum oven 95° C. for 24 hr) to produce a flat-plate-shaped base material. Then, paper filters were set in contact relation on the surfaces (upper and lower surfaces) of the base material. This base material was immersed in a monomer solution composed of the same raw materials as those of the base material for 96 hours so that voids formed in the base material were impregnated with the monomer. The base material having been impregnated sufficiently with the monomer was taken out from the monomer solution and the paper filters were taken off, and the surfaces were lightly wiped to remove the monomer therefrom. Succeedingly, glass plates each having a thickness of 1 mm were set on the surfaces (upper and lower surfaces) of the base material. After the air remaining between the glass plates and the base material was pushed off, the base material was put and held in the dry oven at 90° C. for 24 hours to cause polymerization. After the polymerization, the glass plates were removed from the base material. This base material was let stand in the vacuum oven at 95° C. for 24 hours to bring the second polymerization to completion.

The base material produced by the two-stage polymerization was cut into a disk having a diameter of 10 mm and a thickness of 1 mm. This disk was inspected by the above mentioned glistening inspection to check the occurrence degree of luminescent spots. The constant temperature water bath was previously filled with pure water controlled at 45° C., and the disk was immersed in the water bath for 1 hour. Thereafter, the disk was taken out together with the constant temperature water from the water bath to room temperature and immediately observed through the microscope to check variations with time. This observation was conducted to see the state of the disk after 10 min. and 60 min. respectively from the time the disk was taken out from the water bath.

The results of the appearance checks during the impregnation with the monomer and during the repolymerization in the dry oven, and the glistening inspection were shown in Table 3. In this table, mark ○ designates the case where no defect in appearance such as warps and cracks was found and mark x designates another case where defects in appearance were found.

EXAMPLE 4

Example 4 was performed in the same manner as Example 3 except that aluminum foil was used, instead of the glass plates, as the protective member during the repolymerization of the base material in the dry oven. The materials of the monomer solution used in this example were the same as those in Example 3. The same appearance checks and glistening inspection as those in Example 3 were conducted. The results are shown in Table 3.

COMPARATIVE EXAMPLE 2

Comparative example 2 was performed in the same manner as Example 3, except that paper filters or the like for the absorptive members were not used during the impregnation of the base material with the monomer and the base material was placed at the bottom of a vessel filled with the monomer mixed solution so that the base material was impregnated with the monomer in a state that the lower surface of the base material was in contact with the bottom of the vessel. The materials of the base material and the monomer solution used in this example were the same as those in Example 3. The same appearance checks and glistening inspection as in Example 3 were conducted.

COMPARATIVE EXAMPLE 3

Comparative example 3 was performed in the same manner as Example 3, except that glass plates or the like were not used for the protective members during the repolymerization of the base material in the dry oven and the polymerization was caused in a state that the surfaces of the base material was exposed to the ambient air. The materials of the base material and the monomer solution used in this example were the same as those in Example 3. The same appearance checks and glistening inspection as in Example 3 were conducted.

TABLE 3

| | Appearance check (During impregnation) | Appearance check (During repolymerization) | Glistening inspection | Comprehensive evaluation |
|---|---|---|---|---|
| Example 3 | ○ | ○ | Very few luminescent spots were found | ○ |
| Example 4 | ○ | ○ | Very few luminescent spots were found | ○ |

TABLE 3-continued

|  | Appearance check (During impregnation) | Appearance check (During repolymerization) | Glistening inspection | Comprehensive evaluation |
|---|---|---|---|---|
| Comp. Ex. 2 | X | ○ | Very few luminescent spots were found | X |
| Comp. Ex. 3 | ○ | X | Very few luminescent spots were found | X |

(Results)

Very few luminescent spots were found in all Examples 3 and 4 and Comparative examples 2 and 3, and warps of the base material were found during the impregnation in Comparative example 2. In Comparative example 2, furthermore, cracks were generated in the surfaces of the base material during repolymerization in the dry oven.

According to the present invention, it is possible to prevent the formation of voids in a lens base material while keeping a good lens material condition.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A method of manufacturing an intraocular lens of a soft type which is foldable, including:
   a first step of making a first monomer mixed solution with plural monomers and polymerizing the plural monomers to produce a base material for the intraocular lens;
   a second step of heating the base material produced in the first step in an oven to terminate polymerization;
   a third step, after the second step, of immersing the base material into a second monomer mixed solution which is the same as the first monomer mixed solution to impregnate the base material with the second monomer mixed solution so that any voids formed in the base material can be filled;
   a fourth step, after the third step, of taking out the base material from the second monomer mixed solution and removing the second monomer mixed solution from a surface of the base material;
   a fifth step, after the fourth step, of heating the base material in an oven to cause repolymerization; and
   a sixth step, after the fifth step, of forming the intraocular lens from the repolymerized material.

2. The manufacturing method according to claim 1, wherein the third step includes the steps of:
   setting an absorptive member of a sheet form on the surface of the base material, the absorptive member being capable of absorbing the second monomer mixed solution; and
   immersing the base material on which the absorptive member is set into the second monomer mixed solution.

3. The manufacturing method according to claim 1, wherein the fifth step includes the steps of:
   setting a protective member of a sheet form resistant to heat on the surface of the base material to prevent the surface of the base material from drying; and
   heating the base material on which the protective member is set in the oven.

* * * * *